(12) United States Patent
Baranov (10) Patent No.: US 9,435,787 B2
(45) Date of Patent: Sep. 6, 2016

(54) CELL ANALYSIS BY MASS CYTOMETRY (71) Applicant: Fluidigm Canada Inc., Markham (CA)

(72) Inventor: Vladimir Baranov, Richmond Hill (CA)

(73) Assignee: Fluidigm Canada Inc., Markham (CA)

( * ) Notice: Subject to any disclaimer, the term of this patent is extended or adjusted under 35 U.S.C. 154(b) by 0 days.

(21) Appl. No.: 15/001,589

(22) Filed: Jan. 20, 2016

(65) Prior Publication Data

US 2016/0131635 A1 May 12, 2016

Related U.S. Application Data

(62) Division of application No. 14/060,125, filed on Oct. 22, 2013, now Pat. No. 9,261,503.

(60) Provisional application No. 61/719,087, filed on Oct. 26, 2012.

(51) Int. Cl.
*G01N 15/10* (2006.01)
*G01N 33/483* (2006.01)
*C12M 1/34* (2006.01)
*G01N 33/569* (2006.01)
*G01N 1/04* (2006.01)

(52) U.S. Cl.
CPC .......... *G01N 33/4833* (2013.01); *G01N 15/10* (2013.01); *C12M 1/343* (2013.01); *G01N 33/569* (2013.01); *G01N 2001/045* (2013.01); *G01N 2015/1006* (2013.01); *G01N 2015/1093* (2013.01)

(58) Field of Classification Search
None
See application file for complete search history.

(56) References Cited

U.S. PATENT DOCUMENTS

| 5,885,840 | A | 3/1999 | Kamentsky et al. |
| 7,135,296 | B2 | 11/2006 | Baranov et al. |
| 7,479,630 | B2 | 1/2009 | Bandura et al. |
| 8,003,312 | B2 | 8/2011 | Krutzik et al. |
| 2005/0218319 | A1 | 10/2005 | Bandura et al. |
| 2008/0020474 | A1 | 1/2008 | Hayashizaki et al. |
| 2008/0176332 | A1 | 7/2008 | Berns et al. |
| 2010/0144056 | A1 | 6/2010 | Winnik et al. |
| 2012/0074307 | A1 | 3/2012 | Becker et al. |
| 2012/0077714 | A1 | 3/2012 | Nolan et al. |
| 2014/0120550 | A1 | 5/2014 | Baranov |

OTHER PUBLICATIONS

Bandura et al. "Mass Cytometry: Technique for real time single cell multitarget immunoassay based on inductively coupled plasma time-of-flight mass spectrometry," Analytical Chemistry, 2009, vol. 81, pp. 6813-6822.

Becker et al., "Imaging of copper, zinc, and other elements in thin section of human brain samples (Hippocampus) Laser Ablation Inductively Coupled Plasma Mass Spectrometry", Anal. Chem. 2005, 77, 3208-3216.

(Continued)

*Primary Examiner* — Rebecca Martinez
(74) *Attorney, Agent, or Firm* — Kilpatrick Townsend & Stockton LLP (57) ABSTRACT

A combination of mutually exclusive cell-based analytical techniques can be applied to the same group of cells for analysis. The same group of cells can be prepared for analysis by each technique resulting with candidate cells targeted for mass cytometry analysis. This configuration allows for the correlation of the information between each technique to produce a matrix of multi dimension of cellular information with the same group of cells.

13 Claims, 5 Drawing Sheets

(56) References Cited

OTHER PUBLICATIONS

Becker et al., "Bioimaging of metals in brain tissue by laser ablation inductively coupled plasma mass spectrometry (LA-ICP-MS) and metallomics", Metallomics, 2010,2, 104-111.

De Vries et al., "Photoionization mass spectrometer with a microscope laser desorption source," Review of Scientific Instruments, 1992, vol. 63, pp. 3321-3325.

Gao et al., "Single-cell elemental analysis via high irradiance femtosecond laser ionization time-of-flight mass spectrometry", Anal. Chem. 2013, 85,4268-4272.

Giesen et al., "Multiplezed immunohistochemical detection of tumor markers in breast cancer tissue using laser ablation inductively coupled plasma mass spectrometry", Anal. Chem. 2011, 83, 8177-8133.

Leach et al., "Standardless semiquantitative analysis of metals using single-shot laser ablation inductively coupled plasma time-of-flight mass spectrometry", Anal. Chem., 2001, 73, 2959-2967.

Leach et al., "Factors affecting the production of fast transient signals in single shot laser ablation inductively coupled plasma mass spectrometry", Appl. Spectroscopy., 2002, 56, 62-69.

Leach et al., "Identification of alloys using single shot laser ablation inductively coupled plasma time-of-ftight mass spectrometry", J. Anal. At. Spectrom., 2002, 17, 852-857.

Hutchinson et al., "Imaging and spatial distribution of B-amyloid peptide and metal ions in Alzheimer's plaques by laser ablation-inductively coupled plasma-mass spectrometry", Anal. Biochem, 2005, 346, 225-233.

Seuma et al., "Combination of immunohistochemistry and laser ablation ICP mass spectrometry for imaging of cancer biomarkers", Proteomics 2008, 8, 3775-3784.

Sheng Hong et al., "Detection of multiple proteins on one spot by laser ablation inductively coupled plasma mass spectrometry and application to immunomicroarray with element-tagged antibodies", Anal. Chern., 2007, 79, 923-929.

Shrestha et al., "In situ metabolic profiling of single cells by laser ablation electrospray ionization mass spectrometry", Anal. Chern., 2009, 81, 8265-8271.

Waentig et al., "Multi-parametric analysis of cytochrome P450 expression in rat liver microsomes by LA-ICP-MS", J. Anal. At. Spectrom., 2011,26,310-319.

Wang et al., "ICP-MS-Based strategies for protein quantification", Mass Spectrometry Reviews, 2010, 29, 326-348.

Chery et al., "Detection of metals in proteins by means of polyacrylaminde gel electrophoresis and laser ablation-inductively coupled plasma-mass spectrometry: Application to selenium", Electrophoresis 2003, 24, 3305-3313.

Cellular Information Matrix

| Location | | | Property of Interest | | | | Elemental Tag | | | | |
|---|---|---|---|---|---|---|---|---|---|---|---|
| X | Y | Z | a | b | c | d | T1 | T2 | T3 | ... | Tn |
| 2.5 | 1.9 | 0.5 | yes | no | no | no | $3.2 \times 10^5$ | $2.8 \times 10^5$ | $2.8 \times 10^5$ | | |
| 2.6 | 6 | | yes | no | no | yes | $5.1 \times 10^5$ | | $1.8 \times 10^5$ | | $1.2 \times 10^5$ |
| 2.9 | 6.9 | 0.6 | no | no | yes | yes | | $3.2 \times 10^5$ | $5.3 \times 10^5$ | | |
| 3.2 | 7.3 | 0.5 | no | no | yes | yes | | $4.3 \times 10^5$ | $4.3 \times 10^5$ | | $2.2 \times 10^5$ |
| 3.3 | 7.7 | | yes | no | no | no | $2.8 \times 10^5$ | $2.3 \times 10^5$ | $2.9 \times 10^5$ | | $2.9 \times 10^5$ |
| 4.8 | 9.2 | | no | yes | yes | no | $1.2 \times 10^5$ | $4.6 \times 10^5$ | $1.8 \times 10^5$ | | $1.8 \times 10^5$ |
| 12.3 | 25.3 | | no | yes | yes | no | | $5.1 \times 10^5$ | $1.2 \times 10^5$ | | $3.2 \times 10^5$ |
| 18.1 | 29.8 | | yes | no | no | no | | $4.1 \times 10^5$ | $3.1 \times 10^5$ | | $2.1 \times 10^5$ |
| 18.2 | 42.1 | 0.5 | yes | no | no | no | $1.2 \times 10^5$ | | $3.2 \times 10^5$ | | |
| 19.8 | 48.9 | | yes | no | no | no | $1.8 \times 10^5$ | $2.8 \times 10^5$ | | | $3.6 \times 10^5$ |
| 27 | 52.3 | | yes | no | no | yes | $2.8 \times 10^5$ | $5.1 \times 10^5$ | | | $6.8 \times 10^5$ |
| 28.5 | 52.9 | | no | no | yes | yes | $3.2 \times 10^5$ | | $2.8 \times 10^5$ | | $7.2 \times 10^5$ |
| 29 | 52.9 | | no | no | yes | yes | | $4.5 \times 10^5$ | | | $7.2 \times 10^5$ |
| 40 | 52.9 | | yes | no | no | no | $2.3 \times 10^5$ | | $4.7 \times 10^5$ | | $5.1 \times 10^5$ |
| 40.2 | 52.9 | 6 | no | yes | yes | no | | $1.2 \times 10^5$ | $3.2 \times 10^5$ | | $1.7 \times 10^5$ |

CELL ANALYSIS BY MASS CYTOMETRY

This application is a divisional of U.S. application Ser. No. 14/060,125, filed on Oct. 22, 2013, which claims the benefit of U.S. Provisional Patent Application Ser. No. 61/719,087, filed Oct. 26, 2012, the entire contents of which are incorporated by this reference.

FIELD

This invention relates to apparatus and methods for cell analysis by mass cytometry.

INTRODUCTION

One area of cell biology research involves the interrogation of cellular samples by the identification of biological properties indicative of a cell function, cellular processes or a response due to certain reactions. Some of these properties can be observed with traditional cell-based imaging techniques such as microscopy for visualizing the appearance of structural features of the cell or by visualizing markers in immunocytochemistry and immunohistochemistry utilizing luminescent or radioactivity detection.

Alternatively, a technique for single cell analysis using mass cytometry can be applied to cells labeled with metal conjugated antibodies and metallointercalators and introduced individually into an Inductively Coupled Plasma (ICP) ion source, where the cells are vaporized, atomized and ionized for simultaneous elemental analysis. As a consequence of the large number of distinguishable element tags and the simultaneous detection and quantification by the mass cytometer, the cellular properties determined by this multiplexed technique can be used to extend the dimension of cellular analysis above the capabilities of the traditional cell-based imaging or visualization techniques.

However, the cell-based imaging/visualizing techniques and the mass cytometry techniques require separate and dedicated sets of cell samples for their analysis. Thus, combining the results of the various independent cellular analysis techniques based on discrete samples to increase the dimension of cellular information can be subjected to inherent uncertainties.

SUMMARY

In view of the foregoing and in accordance with the present teachings, the applicants recognize that a multi dimension analysis of a group of cells can be performed with a combination of techniques by taking advantage of the fact that each technology perform their interrogation based on different processes. A group of cells can be initially prepared according to the conditions required by each technique so that each process can be accumulatively applied to the same group of cells, according to each property of interest, without substantial interference from the conditions imposed by each process. The sequence for the interrogation processes can be selected in the order which tends to preserve the conditions for each subsequent technique, resulting with the interrogation performed by the mass cytometry detector for the final investigation. A laser ablation mass cytometry process can be configured to target only candidate cells that have been previously identified as having properties of interest. A direct correlation between the results from the mass cytometry analysis for each candidate cell and the corresponding properties of interest can be established for the same group of cells.

Another aspect of the teaching is a method for cellular analysis by mass cytometry. The method includes providing a group of cells labeled with more than one distinct elemental tag and selecting a candidate cell in the group of cells by identifying the location of the candidate cell having a property of interest. The location of the candidate cell according to its position within the group of cells is recorded such that when at least one laser pulse is directed onto the candidate cell at the recorded location a discrete plume for each of the at least one laser pulse is generated. Each of the discrete plume comprises the more than one distinct elemental tag. The method further comprises introducing each of the discrete plume into an inductively coupled plasma and generating groups of elemental ions corresponding with each of the more than one distinct elemental tag which can be simultaneously detected by mass cytometry for each discrete plume. The detected elemental ions are correlated with the property of interest.

Yet another aspect of the teaching is an elemental tagged cell analysis system. The system has at least one interrogator configured to identify the location of a candidate cell and a data source formatted to record the location of the candidate cell. A laser ablation system is interfaced with the data source in which the laser ablation system is configured to direct at least one laser pulse at the location of the candidate cell. The system further comprises a mass cytometer coupled to the laser ablation system in which the mass cytometer is configured to detect the elemental tag associated with the candidate cell.

DRAWINGS

The skilled person in the art will understand that the drawings, described below, are for illustration purposes only. The drawings are not intended to limit the scope of the applicant's teachings in any way. In the accompany drawings, in which like reference numerals indicate like parts.

DESCRIPTION OF VARIOUS EMBODIMENTS

Figure 1:
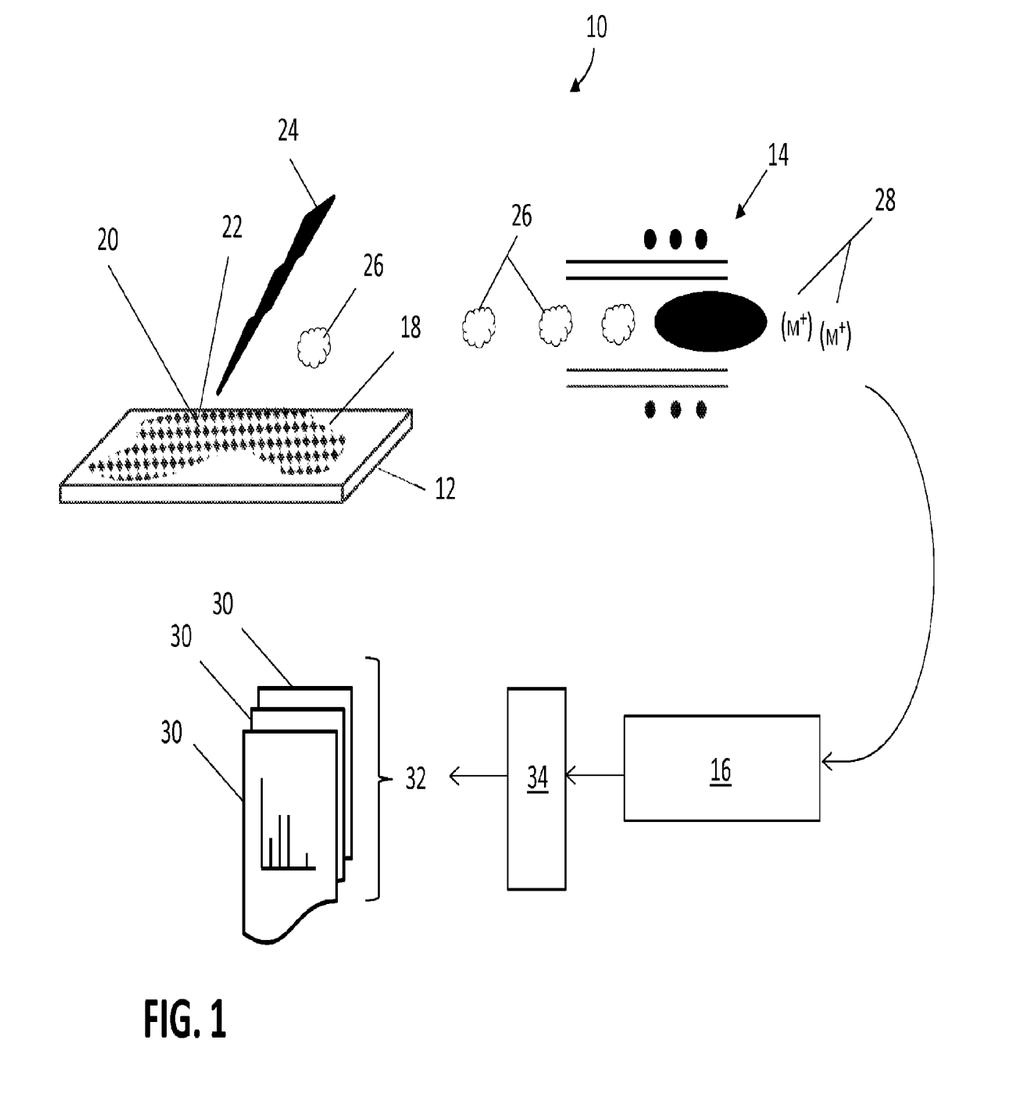
FIG. 1 is a pictorial representation of the system and process according to one embodiment of the present teaching.
Figure 1A:
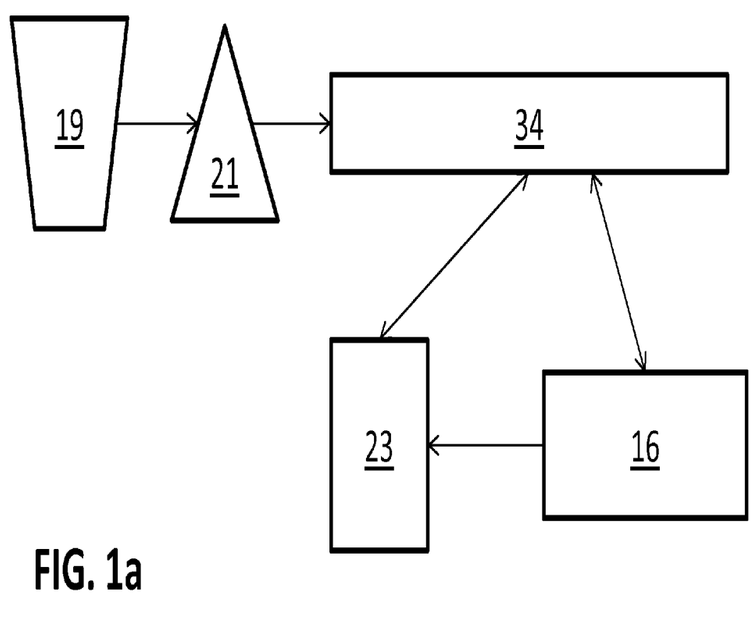
FIG. 1A is a schematic diagram of the system illustrated in FIG. 1.

It should be understood that the phrase "a" or "an" used in conjunction with the present teachings with reference to various elements encompasses "one or more" or "at least one" unless the context clearly indicates otherwise. Reference is first made to FIG. 1, which shows a pictorial representation of the cellular analysis system, generally indicated by reference number 10. The cellular analysis system 10 comprises a base 12 coupled to an inductively coupled plasma (ICP) ion source 14 of a mass cytometer 16. Generally, the ICP ion source 14 can be considered as an integral component of the mass cytometer 16, however for clarity, the ICP ion source 14 is represented separately from the mass cytometer 16. The base 12, a glass microscope slide for instance, provides a surface that can be configured to hold a group of cells 18, from which candidate cells 20 can be identified, or have been identified by an interrogator 19, as having properties of interest and subsequently for analysis by the mass cytometer 16. The cellular analysis system 10 further comprises a laser ablation system 23 for supplying at least one laser pulse 24 directed at the candidate cell 20 at its location 22 within the group of cells 18. The mass cytometer 16 can comprise a control system 34 for controlling the laser ablation system and for generating corresponding elemental tag data 30. A schematic of this system is illustrated in FIG. 1A.

Generally, in mass cytometry, for simultaneous multi parameter analysis within a single cell, a group of cells 18 can be labeled with more than one distinct elemental tag Tn. The distinct elemental tag Tn can be typically selected from the group comprising transitional metals as described in co-pending U.S. patent application Ser. No. 12/513,011, published as US2010/0144056, assigned to the assignees of the present teachings. For convenience, the "n" notation in Tn can be a variable to signify the different transitional elementals or metal isotopes. In various embodiments, for example, a group of cells 18 can be labeled with more than one affinity reagents, such as in the case of the different types of elemental conjugated antibodies where each type of antibody being tagged with one or more distinct elemental tag Tn. The distinct metal or elemental tag Tn conjugated to each type of antibody can be a metal isotope of any one or a combination of Gd, Nd, Tb, Eu, Gd, Dy, Ho, Sm, Er, Yb, to name only a few. Each type of elemental conjugated antibodies can be uniquely distinguishable by its distinct elemental tag Tn. As generally known, the cells in the group of cells 20 which express an affinity to the metal conjugated antibody can remain labeled with the more than one elemental tag Tn. Thus, upon elemental analysis by the mass cytometer 16, the elemental signature of the cell is represented by the distinct element tags Tn associated with the antibodies.

Figure 2:
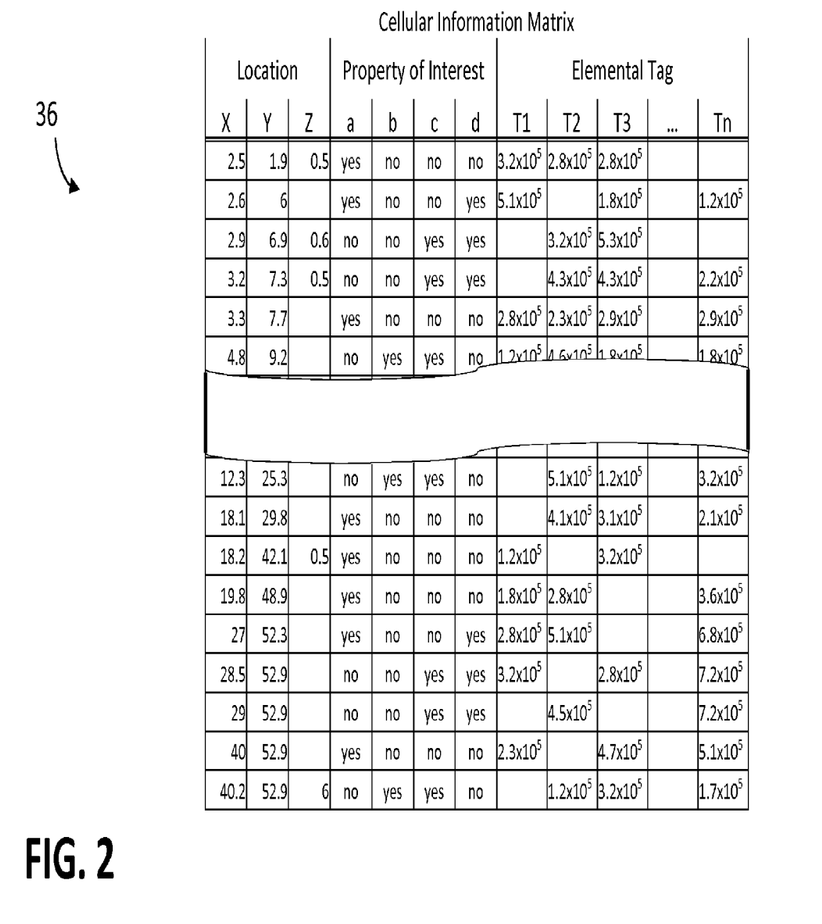
FIG. 2 is an exemplary matrix containing the multi dimension cellular information according to the present teaching.

As noted above, the applicants of the present teachings recognizes that the interrogation process for detecting different properties of interest can be combined in a multi dimension cellular analysis with the same group of cells 18 according to the provision that a) at the outset, the group of cells exhibit or can be prepared with the condition(s) to exhibit the property of interest corresponding with each interrogation process; b) the sequence of analysis can be selected to maintain the integrity of each property of interest for subsequent interrogation process; and c) the results from each analysis can be cross correlated. Since the labeled cells containing the elemental tag(s) is vaporizes during ionization by the ICP ion source 14, the mass cytometry detection process can be the basis of the final interrogator of the multi dimension cellular analysis. Accordingly, the labeled group of cells 18 can undergo initial interrogation processes to identify the candidate cells 20 having properties deemed to be of interest, other than those associated with the more than one distinct elemental tag Tn. In various embodiments, for example, a property of interest can be a viability determination to identify candidate cells 20 that can be either live or dead and, another property of interest can be based on the physical shape or a physical feature inherent in the live or dead candidate cell. A further property of interest, dependent or independent of either of the aforementioned property of interest can, for example, correspond with other luminescent properties associated with the condition of immunostaining techniques to identify candidate cells with certain proteins of interest. Thus, it is anticipated that each property of interest can be represented by its specific physical location(s) within the same or different candidate cells 20. Although the process of the initial interrogation disclosed generally correspond with optical or fluorescence microscopes, other cell-based imaging/visualizing type of interrogators 19 such as that employing electron or confocal microscopes have been considered and that their use can be applied independently or in combination thereof. Thus for the candidate cell section process, the initial interrogation can be performed by at least one interrogator 19 adapted to identify candidate cells with corresponding properties of interest. Once the candidate cells 20 have been identified, the location of the candidate cells 20, as can be defined by its coordinates, with respect to their position within the group of cells 18 can be recorded against each property of interest independently or in combination thereof. As illustrated in FIG. 2, he information in a data source 21 concerning the candidate cell's location 22 and the corresponding properties of interest can be coded in a format which can be accessible by the control system 34 and can be made part of the matrix containing the multiple dimension of cellular information 36.

Subsequently, by having access to the information in the data source 21, for each recorded location 22, the control system 34 can direct at least one laser pulse 24 onto the corresponding candidate cell 20 so that some of the cell material in the form of a discrete plume 26 can be removed. Generally, each laser pulse can generate a discrete plume 26 so that a series of laser pulses can generate a series of corresponding discrete plumes 26. Consequently, the material removed from the candidate cell 20 for each discrete plume 26 can contain the more than one distinct elemental tag Tn. Upon mass cytometry analysis, the detection of the more than one distinct elemental tag Tn from the candidate cell 20 can represent the presence of the associated affinity reagent and can be correlated with the property of interest for the candidate cell 20, as exemplified in FIG. 2.

While maintaining the spatial separation of each successive plume 26, each plume 26 can be transported and introduced into the ICP ion source 14 as discrete and independent entities. As each discrete plume 26 passes into the ICP ion source 14, each elemental tag Tn can be ionized into corresponding elemental ions quantitatively related to each elemental tag Tn. Since there can be more than one distinct elemental tag Tn in the candidate cell 20, the ICP ion source 14 can generate a distinct group of elemental ions for each elemental tag Tn. Consequently, for each discrete plume 26, the ICP ion source 14 can generate groups of elemental ions 28, represented generally as ($M^+$) in FIG. 1. Each of the groups of elemental ions 28 can be detected by the mass cytometer 16, according to the ions' mass to charge ration (m/z). In accordance with the present teachings, the mass cytometer 16 can detect each type of elemental ions simultaneously and, with the advantage of a fast ion transit time for minimizing overlap, the mass cytometer 16 can differentiate between groups of elemental ions originating from successive lasers pulses. The elemental tag data 30, shown in FIG. 1 as a succession of single data files in a total set 32 of data, represents the data acquired from simultaneously detecting the groups of elemental ions 28 for the succession of each plume 26. Hence, the cellular analysis system 10 can detect and identify each of the more than one distinct elemental tag Tn simultaneously for each laser pulse 24 and generate elemental tag data 30 that can be recorded against the candidate cell's property of interest.

While generally, a single laser pulse 24 can completely ablate a candidate cell 20 and generate a plume containing the more than one distinct elemental tag Tn, there can be some instance of candidate cells 20 requiring a series of laser pulses 24 to penetrating into the cell, or through an adjacent surface, in order to achieve maximum intensity of the more than one distinct elemental tag Tn. Furthermore, cellular profiling can be achieved with an appropriate laser configuration having the capability of delivering energy with temporal and spatial precision. A number of laser pulses 24 can be used to resolve the elemental tag Tn contained within the candidate cell 20. For instance, during the analysis, as each laser pulse 24 removes sequential layers of the labeled candidate cell 20, groups of elemental ions 28 corresponding with the more than one distinct elemental tag Tn can be simultaneously detected by the mass cytometer 16. Each of the detected groups of elemental ions 28 can represent the material removed at each layer of the candidate cell 20. As noted above, some of the discrete plumes 26 can contain no metal elements or some of the discrete plumes 26 can comprise a progression of metal elements of various concentrations. Thus, for each of the simultaneous measurements performed by the mass cytometer 16, the data 30 in the set 32 can contain qualitative and quantitative information based on the presence and in some instances the absence, of the one or more elemental tag Tn. Each of the acquired data 30 can provide a piece of the information about the cross-section or thickness profile of the labeled candidate cell 20.

Figure 3:
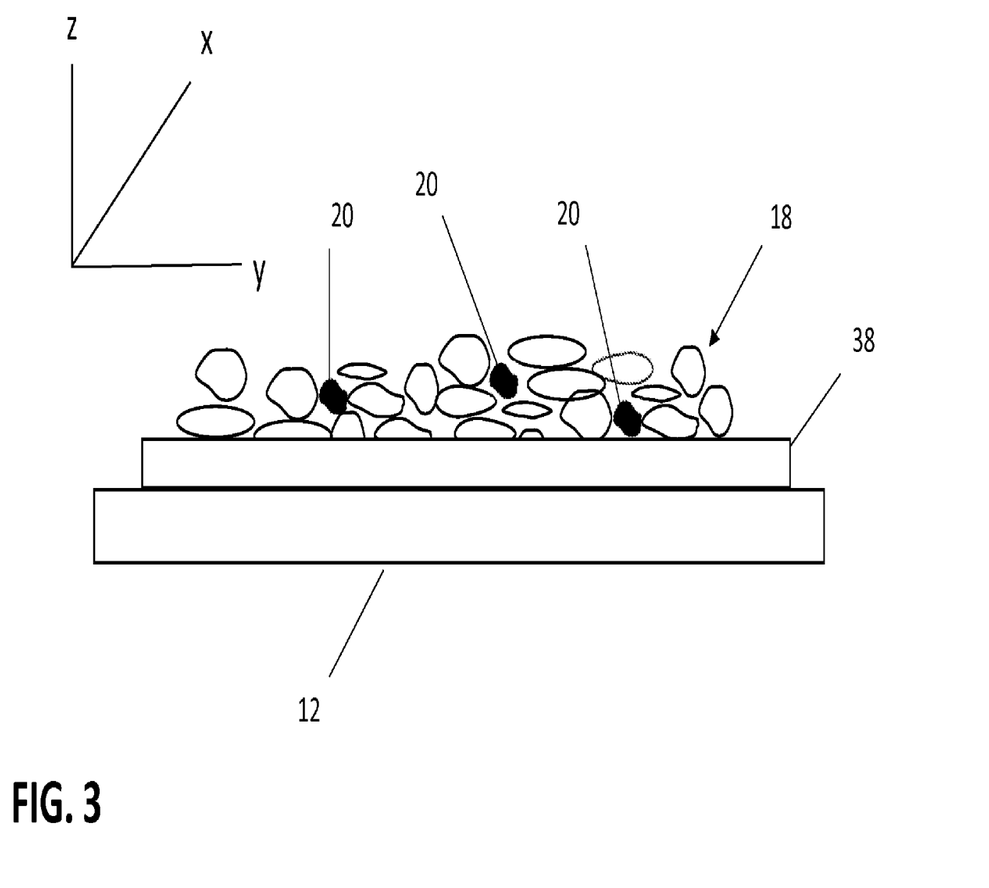
FIG. 3 is close up view of the base according to an embodiment of FIG. 1.

Furthermore, there can be instances where, for example, the thickness to the group of cells 18 is greater than an average cell diameter such as in the case of overlapping layers of cells in the presence of cell medium or in the case of thick tissue sections or unsectioned whole tissue specimen, as generally indicated in FIG. 3. Consequently, the location of one or more of the identified candidate cell 20 or a part of a candidate cell 20 can be embedded at some distance from either the top or bottom surface of the group of cells 18. In various embodiments for example, the embedded candidate cell or cells 20 can be identified by fluorescence microscopy using a confocal microscope technique to provide localized cell structural images. Other techniques for selecting the candidate cells 20 can be based on identifying their property of interest can comprise of a phosphorescence, a reflection, an absorption, to name only a few. Hence, the location or the local details of the embedded candidate cell or cells 20 can be defined by, for example, a Cartesian coordinate system in 3-dimensional space, (X,Y, Z), where the value for the Z axis in FIG. 3 denotes the depth within the thickness of the group of cells 18. The 3-dimensional coordinates can be recorded (as exemplified in FIG. 2) and used to represent and identifying the location of the candidate cell 20 with respect to its position within the group of cells 18. In this instance, when the location 22 of the candidate cell 20 undergoes the elemental tag Tn analysis technique in accordance with the present teaching, the depth coordinate Z can be regarded as a property of interest and can be used to indicate the expected number of laser pulses 24, for example, that can typically be required in order to reach the embedded candidate cell 20. The succession of discrete plumes 26 generated by the succession of laser pulses 24 can contain no elemental tags Tn until the at least one laser pulse 24 reaches the embedded candidate cell 20 at coordinate Z. Conversely, the actual number of laser pulses deployed to reach the candidate cell 20 and to generate plumes containing elemental tag Tn and the detected group of elemental ions 28 can be correlated with the recorded depth Z as a way of cross calibrating the two mutually exclusive cell-based techniques.

While the present teachings are described in conjunction with various embodiments, it is not intended that the present teachings be limited to such embodiments. On the contrary, the present teachings encompass various alternatives, modifications, and equivalents, as will be appreciated by those of skill in the art. For example, the applicants of the present teachings recognize that concurrently with the elemental tag Tn conjugated label, the group of cells 18 can be initially prepared with conditions to exhibit the property of interest detectable by the imaging/visualization process for identifying the candidate cells 20 as generally known in the art. As such, a group of cells 18 can be prepared with fluorophores labeled proteins and/or endogenous expression of fluorescent reporter proteins in addition to the elemental tag Tn conjugated affinity reagents labeling. Additionally, the elemental tag Tn conjugated antibody can be prepared with luminescent characteristic so as to provide dual properties detectable by more than one mutually exclusive cell-based analytical techniques. In various embodiments, for example, a CD34 protein can be tagged with 148Nd elemental isotopes in addition to a fluorescein for labeling in a biological sample suspected of having a certain function. With fluorescence microscopy, the biological sample can be initially examined and, candidate cells expressing CD34 can be identified and isolated on the glass microscope slide. The location of the isolated CD34 expressed candidate cells can be targeted for elemental detection by mass cytometry according to the present teachings. In this example, the detected group of elemental ions 28 can be correlated with the fluorescein detection as a way of providing quantitation or for confirmatory purposes.

In various embodiments, the information recorded for the candidate cell 20, including but not limited to its location 22, can be in various data source formats and can be accessed by the control system 34 using various protocols. For example, a visual representation of the group of cells 18, such as a fluorescence emission image, can be used to identify and represent each candidate cell 20. In this instance, the interface between the data source 21 and the control system 34 can be an optical detection system with appropriate visual recognition software. The software can be configured for determining the location of the candidate cell 20 from the emission image and subsequently for directing the at least one laser pulse 24 at the location of the candidate cell 20. Alternatively, the information recorded can be represented and retrieved by various optical machine-readable interfaces such as that embodied with barcode (1D or 2D) readers/ scanners or through other interfaces that employ radio frequency identification (RFID) or variations and combinations thereof. Furthermore, the location of the candidate cell 20 along with its property of interest can generally be recorded as an alphanumeric data record accessible by the control system 34 or the data can be manually entered into the operating controls of the laser ablation system or the mass cytometry system directly. Irrespective of the interfacing format from which the candidate cell's information is transferred, the configuration of the laser ablation system can be designed so that recorded information can provide the location coordinates for directing at least one laser pulse 24 at the location 22 of the candidate cell 20.

In various embodiments, while the base 12 has been described as a glass microscope slide that is generally consistent with the material requirements for microscopy applications, the applicants have contemplated the base 12 to be made of other material such as one of or a combination of stainless steel, quartz, ceramic, polytetrafluoroethylene (PTFE) and polyetheretherketone (PEEK) to name a few. Alternatively, referring to FIG. 3, the base 12 can be a support or a structure that can be separated from a microscope slide 38 holding the group of cells 18. For instance, in optical microscopy, a group of cells 18 labeled with more than one distinct elemental tag Tn can be mounted on a microscope slide 38 and illuminated from below (for typical transilluminated light microscopy) or illuminated from above through an objective lens (for typical fluorescence microscopy). An image captured by the microscope optics can be used for identifying a candidate cell 20 according to a property of interest, such as a physical shaped or the presence of a fluorescent probe(s) for example. The location of the identified candidate cell 20 along with its property of interest can be recorded to represent information relevant to the cellular analysis of the biological sample. Generally the identification process can be repeated as required so that more than one candidate cell 20 can be located in the group of cells 18. Once the candidate cell 20 or candidate cells 20 have been identified, the microscope slide 38 and its contents can be transferred to the base 12 for supporting thereof. The information regarding the location of each of the candidate cell 20, expressed by Cartesian coordinates represented in either 2-dimensional or 3-dimensional space within the group of cells 18 for example, can be utilized to direct the at least one laser pulse 24 onto the candidate cell 20 for generating the discrete plume 26 for each of the at least one laser pulse 24.

The applicants of the present teachings recognizes that in order for each elemental tag data 30 to correspond with each of the at least one laser pulse 24, the spatial separation of each successive plume 26, and the corresponding ions, during their travel along the path between the base into the ICP ion source 14 and between the ion source 14 and the ion detector of the mass cytometer 16 is maintained. For example, a solid state laser typically used for laser ablation, such as a femtosecond pulsed laser can be configured to operate with a pulse rate between 10 and 100 Hz. At this frequency range, a plume 26 can be generated every 10 to 100 msec. Considering the lower limit, the system 10 would be required to have a maximum delay time of the order of 10 msec. In accordance with various embodiments of the present teachings, the mass cytometer 16 can be characterized as a "flow-through" analytical device comprising a linear ion path with electrostatic lenses and an ion detector capable of parallel elemental ion detection. In this configuration, a delay time in the order of 10 msec can be achieved so that the groups of elemental ions ($M^+$) can undergo acceleration and pass within the mass cytometer 16 for simultaneous detection. Consequently, the likelihood of the ion detector to separately detect each of the groups of elemental ions 28 can be realized.

Figure 4:
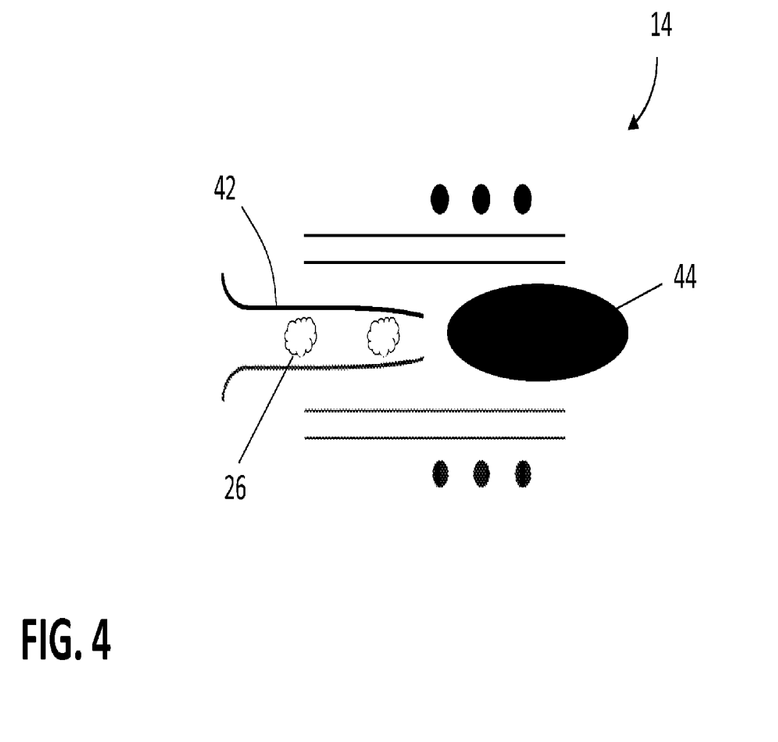
FIG. 4 is a schematic view of an embodiment of the ICP ion source according to the present teaching.

To maintain a corresponding spatial distinctiveness upstream of the mass cytometer 16, the configuration of the path between the laser ablation location, at the base 12, and the entrance to the plasma can be chosen to maximize the plume 26 separation while minimizing flow turbulence. At the lower limit, a delay time of the order of 10 msec for maintaining the separation of each plume 26 before ionization can be achieved with a path having a minimum distance of plume travel and a corresponding means of accelerating the same. Generally, the ICP ion source 14 utilizes an injector tube 42, as indicated in FIG. 4, and a flow of carrier gas (not shown) can be applied appropriately to direct each discrete plume 26 into the plasma 44. Accordingly, the injector tube 42 can be configured to provide a laminar or near laminar flow geometry, having a Reynolds number below 2000 for instance, for receiving the plume 26 and for the carrier gas to flow with the plume 26 such that any turbulence can be minimized. Thus, in various embodiments, the combined delay time corresponding to the total path between the base 12 and the ion source 14 and between the ion source 14 and the ion detector of the mass cytometer 16 can be between 20 msec and 200 msec.

Furthermore, in various embodiments, the base 12 can be positioned relative to the ICP ion source 14 such that the travel time for each plume 26 can be minimized. For example, the ICP ion source 14 can be structured to encompass the base 12 for providing a closely coupled laser-ablation-ICP ion source. The laser-ablation-ICP ion source can be configured with an integrated enclosure having an optical entrance for the laser pulses 24, a carrier gas for capturing and transporting the plume and the ICP ion source for generating the groups of elemental ions 28. The carrier gas flow can be configured to sweep off each discrete plume 26 at the ablation location 22 and pass each plume 26 directly into the plasma 44.

While in various embodiments the term "group of cells" is generally in reference to cells contained in thinly sectioned biological tissue samples or unsectioned tissue whole specimens, the present teachings can be equally applied to cells typically found in cell cultures. In various embodiments, the group of cells 18 can be a mixture of cell subgroups where each subgroup can originate from different sources or different biological entities. In this instance, the cell's origins can be characterized by one of the properties of interest. For example, consider samples taken from more than one biological entity where each sample corresponds with a cell subgroup that can be distinctly labeled with more than one distinct elemental tag Tn. Each of the cell subgroups can be combined into the same group of cells 18 so that the cells from each sample can collectively express its distinctly labeled elemental conjugated antibody within the same group of cells 20. The combined group of cells 18 can be interrogated and candidate cells 20 can be identified and selected based on some property of interest without knowledge of the candidate cell's origin. Upon elemental analysis according to the present teachings, the elemental tags Tn can be detected and the corresponding candidate cells 20 can be identified as being related to the specific biological entity. Accordingly, the relation between the property of interest and the detected elemental ions 24 can be correlated to determine the property of interest indicative of that cell subgroup and potentially the cell's origin. Generally, the advantage of the present teachings can be applied to groups of cells comprising non-disrupted cells where non-disrupted candidate cells can be identified and further analyzed for its elemental tags by mass cytometry.

While efforts have been described to create the conditions for maintaining the spatial separation of each plume 26 and the corresponding groups of elemental ions 28 throughout the cellular analysis, the applicants of the present teachings recognizes that some spatial spreading or overlapping can be present. Accordingly, the applicants have contemplated an averaging approach applied to two or more of the acquired elemental data 30 without substantial loss to the information generated from each laser pulse 24. Alternatively, an integrated approach of combining each of the acquired elemental data 30 into the set 32 can be sufficient to represent the mass cytometry information portion of the multi dimension cellular analysis. In various embodiments, a data analysis algorithm, such as FFT, can be used for de-convoluting the integrated data set 32. Different forms of algorithms can be operated within the analysis system 10 or can be applied post data acquisition as is generally known.

Furthermore, the control system 34 can be configured to serve multifunctional purposes in accordance with the present teachings. Although the control system 34 has been described in connection with controlling the laser ablation system and for generating corresponding elemental tag data 30, the control system 34, typically functioning under logic control, can provide various levels of automation or to perform a sequence of feedback controlled actions to enable the analysis system 10 to be automated. In various embodiments, for example, the control system 34 can be a processor driven system coupled with a automated sample handling system to perform the interrogation and identification, the information recording and accessing, the directing of the laser pulses, the mass cytometry detection process and the data correlation autonomously or with user intervention.

The invention claimed is:

1. A method for cellular analysis by mass cytometry comprising:
   providing a group of cells labeled with more than one distinct elemental tag;
   selecting a candidate cell in the group of cells by identifying a location at the candidate cell, the candidate cell having a property of interest;
   recording the location at the candidate cell;
   directing at least one laser pulse onto the candidate cell at the recorded location and generating a discrete plume for each of the at least one laser pulse, each of the discrete plume comprises the more than one distinct elemental tag;
   introducing each of the discrete plume into an inductively coupled plasma and generating groups of elemental ions corresponding with each of the more than one distinct elemental tag;
   detecting each of the groups of elemental ions simultaneously for each of the discrete plume by mass cytometry; and
   correlating the detected elemental ions with the property of interest.

2. The method according to claim 1 in which providing the group of cells labeled with more than one distinct elemental tag comprises labeling the group of cells with more than one elemental conjugated antibody, each of the more than one elemental conjugated antibody comprising one or more distinct elemental tag.

3. The method according to claim 2 in which the one or more distinct elemental tag is selected from a group comprising transitional metals.

4. The method according to claim 3 in which correlating the detected elemental ions with the property of interest comprises generating elemental tag data from the detected elemental ions and recording the elemental tag data against the property of interest.

5. The method according to claim 4 in which the group of cells comprises more than one cell subgroup, each cell subgroup labeled with more than one distinct elemental tag.

6. The method according to claim 5 further comprising identifying the more than one cell subgroup according to the property of interest.

7. The method according to claim 6 in which the property of interest is identified by one or more of a fluorescence, a phosphorescence, a reflection, an absorption, a shape recognition, a physical feature, or a combination thereof.

8. The method according to claim 4 further comprising representing the location at the candidate cell in two-dimensional space within the group of cells.

9. The method according to claim 4 further comprising representing the location at the candidate cell in three-dimensional space within the group of cells.

10. The method according to claim 8 further comprising preparing the group of cells with the property of interest.

11. The method according to claim 10 in which the property of interest is identified by one or more of a fluorescence, a phosphorescence, a reflection, an absorption, a shape recognition, a physical feature, or a combination thereof.

12. The method according to claim 10 in which the candidate cell is identified by fluorescent emission.

13. The method according to claim 12 in which the group of cells is a tissue sample.

* * * * *